United States Patent [19]

Drue

[11] Patent Number: 4,608,989
[45] Date of Patent: Sep. 2, 1986

[54] STAND-OFF CELL FOR AN ULTRASONIC SCANNER HEAD

[75] Inventor: Herbert R. C. Drue, Odense, Denmark

[73] Assignee: Medical Innovation Company A/S, Herley, Denmark

[21] Appl. No.: 662,297

[22] PCT Filed: Feb. 7, 1984

[86] PCT No.: PCT/DK84/00011
§ 371 Date: Sep. 21, 1984
§ 102(e) Date: Sep. 21, 1984

[87] PCT Pub. No.: WO84/03034
PCT Pub. Date: Aug. 16, 1984

[30] Foreign Application Priority Data

Feb. 7, 1983 [DK] Denmark ............... 511/83

[51] Int. Cl.⁴ ............................................. A61B 10/00
[52] U.S. Cl. ............................. 128/660; 73/644
[58] Field of Search ....................... 128/660–663, 128/24 A; 73/644, 642

[56] References Cited

U.S. PATENT DOCUMENTS

| | | | |
|---|---|---|---|
| 3,269,173 | 8/1966 | Ardenne | 128/660 |
| 3,556,079 | 1/1971 | Omizo | 128/24 A |
| 3,721,227 | 3/1973 | Larson et al. | 128/24 A |
| 4,058,114 | 11/1977 | Soldner | 128/660 |
| 4,184,094 | 1/1980 | Kopel | 128/660 |
| 4,185,501 | 1/1980 | Proudian et al. | 128/660 |
| 4,185,502 | 1/1980 | Frank | 128/660 |
| 4,207,901 | 6/1980 | Nigam | 128/660 |
| 4,237,901 | 12/1980 | Taenzer | 128/660 |
| 4,274,421 | 6/1981 | Dory | 128/660 |
| 4,325,381 | 4/1982 | Glenn | 128/660 |
| 4,363,326 | 12/1982 | Kopel | 128/660 |
| 4,402,324 | 9/1983 | Lindgren et al. | 128/660 |
| 4,420,979 | 12/1983 | Momii et al. | 73/644 |
| 4,435,985 | 4/1984 | Wickramasinghe | 73/644 |

FOREIGN PATENT DOCUMENTS 0004845 10/1979 European Pat. Off. ......... 128/24 A

*Primary Examiner*—Kyle L. Howell
*Assistant Examiner*—Ruth S. Smith
*Attorney, Agent, or Firm*—Kenyon & Kenyon

[57] ABSTRACT

A stand-off cell for an ultrasonic scanner head has a slit in which a biopsy needle can be guided. The whole introduction will therefore take place in the area supervisable by the scanner head so that the needle can be guided in a secure manner when making a biopsy. The stand-off cell can be made of a plastics with the same acoustic impedance as tissue and can therefore be manufactured very cheaply. After the needle is introduced the stand-off cell can be removed as the needle slides out through the slit. This makes the biopsy easier and makes it possible to utilize the scanner head in the best way.

12 Claims, 7 Drawing Figures

STAND-OFF CELL FOR AN ULTRASONIC SCANNER HEAD

BACKGROUND OF THE INVENTION

1. Field of the Invention

The invention relates to a stand-off cell for an ultrasonic scanner head which stand-off cell is mounted so that is can be disconnected, on the scanner head by a clutch facing and is in contact with the patient through a contact surface and which furthermore has a number of free surfaces.

2. Description of Related Art

In medical diagnostics one is often interested in making a so-called biopsy. I.e. that one by means of a needle takes a sample from the patient. The placing of the needle is often critical, wherefore one is interested in being able to determine this exactly. This applies for example when taking samples of the amniotic fluid.

The supervision of the placing of the needle has been tried by means of ultrasonic scanning where emitted ultrasonic impulses are reflected from the needle and its surroundings and are used for making pictures i.e. by means of a micro computer and a cathode ray tube.

Ordinary scanner heads consist of a row of transducer elements placed in line. As an example one can mention the scanner head which is described in U.S. Pat. No. 4,346,717. Such scanner heads have the drawback, when used for biopsy that one cannot supervise the first 20-50 mm of the area into which the needle is introduced. This is due to the fact that the needle first has to be led diagonally in under the scanner head before it gets into its supervision area.

In order to avoid this drawback it is known from for example German Patent Specification No. 2.906.474 to use special biopsy heads. They consist of an ordinary linear scanner head through which a canal for introducing the needle has been made. However, in order to make room for this canal one has to remove a number of transducer elements in the center of the head. This creates an area that the scanner head is unable to supervise and this will often be inconvenient when introducing the needle. These special biopsy heads furthermore have the drawback that they are very expensive. They cost even more than a normal scanner head.

If one wishes to supervise an area ultrasonically, which area lies close to the surface of the body, it is furthermore known from for example British Patent Application No. 2.009.563 to use a spacer unit between the scanner itself and the body.

SUMMARY OF THE INVENTION

The aim of the invention is to disclose a stand-off cell for a conventional scanner head so that this will be capable of supervising the whole course of the needle in the patient at a biopsy and this is according to the invention achieved in that the stand-off cell is provided with a slit for engaging a needle or a hypodermic needle and that the slit extends between the contact surface and one of the free surfaces.

As the stand-off cell is made of a material with almost the same acoustic impedance as tissue it will be possible to register the whole course of the needle through this. Due to the slit the needle will first penetrate into the patient in a place which lies within the supervision area of the scanner head. In that the needle is placed in a slit it is furthermore achieved that the scanner head with the stand-off cell can be removed from the needle without pulling the needle out of the patient. This makes it possible to perform an easier biopsy just as it makes it possible to utilize the scanner head better. This is now only used during the placing of the needle itself. The stand-off cell can in a simple manner be made of a suitable plastics, and will therefore be very cheap. Thus it becomes possible to be free to dispose of a suitable number of stand-off cells which makes it possible to use any scanner head optimum for many different purposes.

A stand-off cell according to the invention is characterized in that the contact surface is parallel with the clutch facing. (By "clutch facing" is meant the face of the standoff cell which contacts the scanner head.) For many purposes this is a suitable and very simple execution of a stand-off cell.

If the stand-off cell has one or more reflection surfaces it becomes possible to make stand-off cells where the ultrasonic wave course is "broken" inside the stand-off cell. This can be convenient where the biopsy has to be made in places not very accessible.

A stand-off cell according to the invention can be characterized in that the contact surface stands at right angles to the clutch facing. If the ultrasonic waves are now sent horizontally against a reflection surface, which makes up an angle of 45° at the contact surface, a 90° deflection of the ultrasonic waves is obtained. Thus it becomes possible to introduce a needle in the center of an ultrasonic field under a large number of angles, and for example also at a right angle to the contact surface.

By mounting a guide organ in front of the needle a good control of this is obtained.

By using guide organs which can be disconnected and are adjustable it is obtained that the needle easily can be placed in well-defined angles in proportion to the contact surface, and that the stand-off cell in a simple manner can be removed from the needle.

It may be expedient to make the slit in a needle-guide organ which is secured to the stand-off cell so that it can be disconnected, so the scanner head itself with the stand-off cell can easily be removed from the needle and the needle-guide organ.

BRIEF DESCRIPTION OF THE DRAWINGS

The invention will in the following be described more closely with a reference to the drawing, where.

DESCRIPTION OF THE PREFERRED EMBODIMENTS

Figure 1:
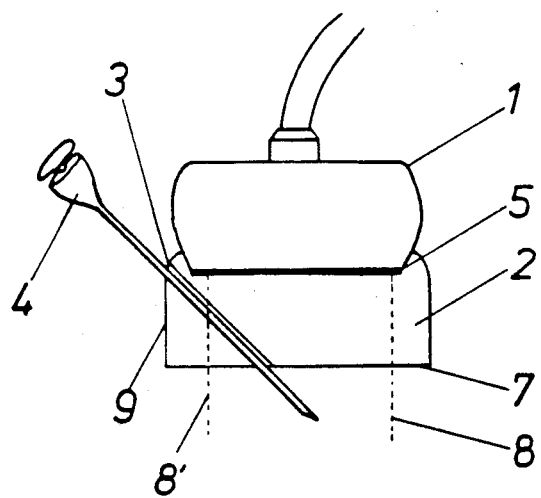
FIG. 1 shows a scanner head with a stand-off cell according to the invention.

On FIG. 1 an ordinary scanner head 1 is seen. To this there is attached a stand-off cell 2 according to the invention at the clutch facing 5. Between the stand-off cell 2 and the scanner head 1 a thin layer of a suitable paste has been put, which ensures a good acoustic clutching between the parts. The same paste can suitably be used between the stand-off cell 2 and the patient.

The stand-off cell 2 is made of a plastics with an acoustic impedance which essentially is the same as that of the patient's tissue. The plastics must furthermore have a poor damping of the ultrasonic waves. It has thus turned out that elastic materials often have a too large damping of the ultrasonic waves wherefore the stand-off cell can be made of a possibly liquid-filled plastics. So one can obtain an efficient transmission of acoustic energy without inconvenient reflections at the transition between the surfaces.

The biopsy needle 4 is led through the slit 3 which is designed between the free side face 9 and the contact surface 7. As can be seen from FIG. 1 the needle first enters the patient in the supervision area of the scanner head which is defined by the lines 8 and 8' on FIG. 1. The slit 3 furthermore supports the needle 4 during its introduction into the patient. When the needle 4 is fully introduced one can without further measures remove the scanner head 1 and the stand-off cell 2 as the needle can be removed through the slit.

The shape of the stand-off cell can be very simple, which makes a very cheap production of it possible, e.g. by machining processes. Moreover, it will be simple to produce stand-off cells for any conceivable scanner head.

Figure 2:
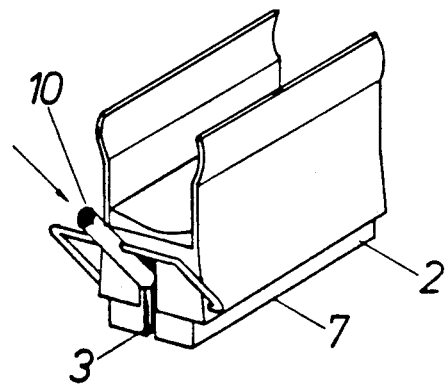
FIG. 2 shows a stand-off cell according to the invention with guide organs for the needle.

On FIG. 2 it can be seen how a stand-off cell 2 according to the invention can be supplied with needle-guide organs 10. These can e.g. consist of a tube with a strap for supporting the needle. Hereby a very safe guiding of the biopsy needle is made possible. The guide organs 10 can be adjustable at various angles with the contact surface, and can of course be made in many other ways than the one shown here. If the needle-guide organs 10 are connected to the stand-off cell 2 in such a manner that they can be released, said stand-off cell will be capable of being released for other use without removing the biopsy needle from the patient.

Figure 3:
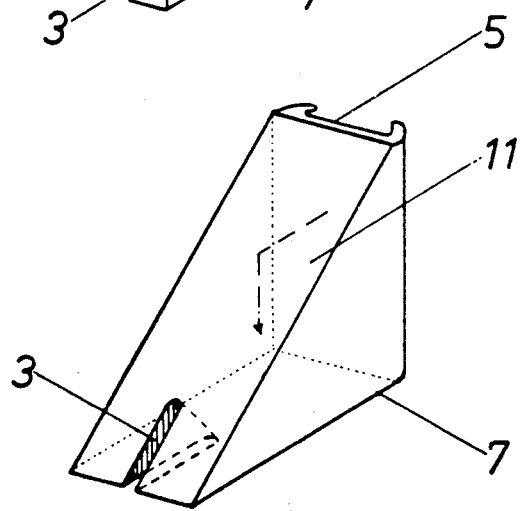
FIG. 3 shows a second embodiment for a stand-off cell according to the invention.

On FIG. 3 a stand-off cell is seen, where the contact surface 7 and the clutch facing 5 stand at right angles to each other.

With different presentation of the slit 3 a large area of variation can be obtained for the angle of the needle by the patient. As the acoustic impedance in air is very different to the acoustic impedance in the stand-off cell, an area, which is turned horizontally against the clutch facing 5 will be deflected 90° of the reflection surface 11. The ultrasonic area will thus be directed vertically down into the patient and it becomes possible to lead the needle vertically down in the center of the sound area. This gives a very precise and efficient control of the needle, and at the same time this embodiment is very material saving.

Figure 4:
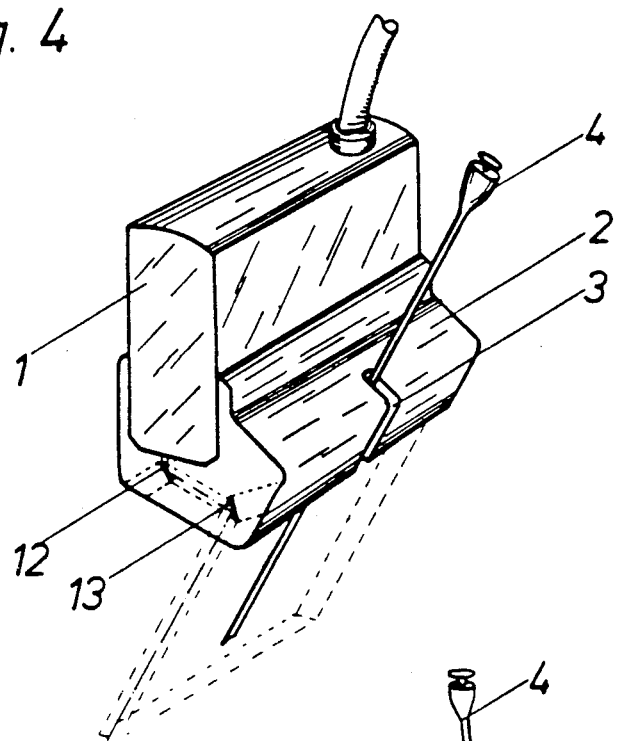
FIG. 4 shows another embodiment for the invention.
Figure 5:
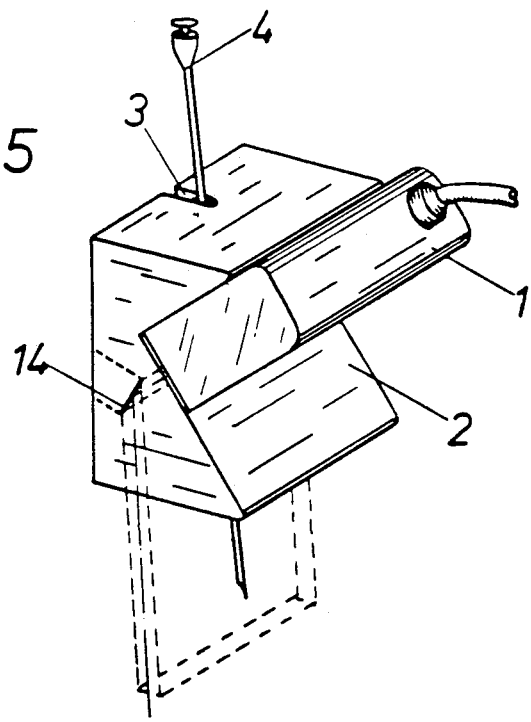
FIG. 5 shows an embodiment for the invention, where the scanner head forms an angle of 45° with the contact surface.

On FIGS. 4 and 5 stand-off cells 2 are seen where the sound area is reflected one or a number of times at the reflection surfaces 12, 13 and 14. It is simple to manufacture such reflection surfaces as they can consist of surfaces for air chambers, openings or metal surfaces. The difference of the acoustic impedance will so ensure total reflection. One can thus manufacture special stand-off cells for places that are difficult to reach or where accuracy is particularly important. It also becomes possible to give the area a favorable direction and to let the needle 4 follow this.

Figure 6:
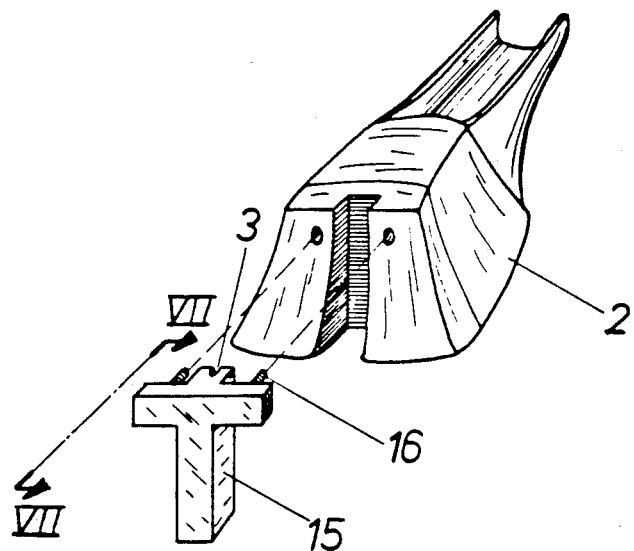
FIG. 6 shows another embodiment for the invention.
Figure 7:
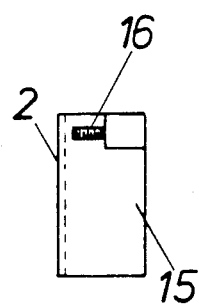
FIG. 7 shows a needle-guide organ seen in section along the line VII—VII on FIG. 6.

On FIGS. 6 and 7 it is seen how the needle can be led in a needle-guide organ 15, which is secured to the stand-off cell 2 by means of pegs and which can be disconnected.

The stand-off cell according to the invention may possibly be made in innumerable ways according to the task the stand-off cell is to be used to perform. The stand-off cell can also easily be adjusted to any scanner head. Thus, it will be possible for a hospital ward to own a large number of scanner heads so that every biopsy can be done quickly and precisely and with a minimum of malaise and risk for the patient.

Finally, it can be added that one could also make use of the fact that the ultrasonic waves at the transition between the stand-off cell and the patient will change course—be refracted—due to the difference in acoustic impedance between the stand-off cell and the tissue. This refraction can be used in such a way that the transducer itself can form an angle which is different from 90° with the patient's skin even if one wishes the ultrasonic waves to penetrate fairly perpendicular into the patient.

Hereby, it becomes possible to lead a hypodermic needle into the patient precisely in the center of the sound area without the needle having to pass through the transducer itself and thus disturb the picture.

I claim:

1. A standoff cell for an ultrasonic scanner head having an area of supervision, the standoff cell comprising:
   clutch facing means for contacting an ultrasonic scanner head;
   contact surface means for contacting a patient's body; and
   an additional surface; and further comprising:
   slit means extending between the contract surface and the additional surface for passage therethrough of a needle, such that the point at which the needle penetrates the patient's body is within the area of supervision of the scanner head.

2. A standoff cell according to claim 1, wherein the contact surface means is parallel to the clutch facing means.

3. A standoff cell according to claim 1, wherein ultrasonic waves emitted by the scanner head pass through the clutch facing means in a direction which would not lead the waves to a location on the contact surface means, through which location the needle passes, the standoff cell further comprising means for reflecting the waves to the location on the contact surface means through which location the needle passes.

4. A standoff cell according to claim 3, wherein the contact surface means stands at right angles to the clutch facing means.

5. A standoff cell according to claim 4, further comprising removable means for retaining the needle in the slit.

6. A standoff cell according to claim 3, wherein the acoustical impedance of the contact surface means differs from that of the patient's body by an amount sufficient to bend at the contact surface means ultrasonic waves emitted from the scanner head to an angle at which it is desired that the ultrasonic waves enter the patient's body.

7. A standoff cell according to claim 1, further comprising guide means for further directing the needle.

8. A standoff cell according to claim 7, wherein the guide means is adjustable.

9. A standoff cell according to claim 7, wherein the guide means is removable.

10. A standoff cell according to claim 9, wherein the acoustical impedance of the contact surface means differs from that of the patient's body by an amount sufficient to bend at the contact surface means ultrasonic waves emitted from the scanner head to an angle at which it is desired that the ultrasonic waves enter the patient's body.

11. A standoff cell according to claim 1, further comprising removable means for retaining the needle in the slit.

12. A standoff cell according to claim 1, wherein the acoustical impedance of the contact surface means differs from that of the patient's body by an amount sufficient to bend at the contact surface means ultrasonic waves emitted from the scanner head to an angle at which it is desired that the ultrasonic waves enter the patient's body.

* * * * *